(12) United States Patent
Besse et al.

(10) Patent No.: US 10,697,936 B2
(45) Date of Patent: Jun. 30, 2020

(54) TSM BIOSENSOR TO EX-VIVO CHARACTERIZE THE VISCOELASTIC PROPERTIES OF SKIN

(71) Applicants: Centre National de la Recherche Scientifique (CNRS), Paris (FR); Universite Cergy-Pontoise, Cergy (FR); Centre de Recherches Biologiques et D'Experimentations Cutanees, Longjumeau (FR)

(72) Inventors: Régis Besse, Saint Pierre des Corps (FR); Jean-Yves Le Huerou, Montreuil (FR); Stéphane Serfaty, Acheres (FR); Elian Lati, Vanves (FR)

(73) Assignees: Centre National de la Recherche Scientifique (CNRS) (FR); Universite Cergy-Pontoise (FR); Centre de Recherches Biologiques et D'Experimentations Cutanees (FR)

( * ) Notice: Subject to any disclaimer, the term of this patent is extended or adjusted under 35 U.S.C. 154(b) by 305 days.

(21) Appl. No.: 15/580,355

(22) PCT Filed: Jun. 8, 2016

(86) PCT No.: PCT/EP2016/063083
§ 371 (c)(1),
(2) Date: Dec. 7, 2017

(87) PCT Pub. No.: WO2016/198483
PCT Pub. Date: Dec. 15, 2016

(65) Prior Publication Data
US 2018/0172640 A1   Jun. 21, 2018

(30) Foreign Application Priority Data

Jun. 8, 2015  (EP) .................................. 15020088
Sep. 3, 2015  (EP) .................................. 15306357

(51) Int. Cl.
*G01N 29/02* (2006.01)
*A61B 5/00* (2006.01)
(Continued)

(52) U.S. Cl.
CPC ........... *G01N 29/022* (2013.01); *A61B 5/442* (2013.01); *G01N 29/028* (2013.01);
(Continued)

(58) Field of Classification Search
CPC ......... G01N 29/022; G01N 2291/0256; G01N 2291/0426; G01N 2291/02483;
(Continued)

(56) References Cited

U.S. PATENT DOCUMENTS

2004/0235198 A1* 11/2004 Marx ............... G01N 33/54373
                                                      436/527
2010/0075347 A1    3/2010 Dasaratha et al.
(Continued)

FOREIGN PATENT DOCUMENTS

WO    2012172253 A1   12/2012

OTHER PUBLICATIONS

International Search Report for appln No. PCT/EP2016/063083 dated Sep. 15, 2016, 3 pages.
(Continued)

*Primary Examiner* — Eric S. McCall
*Assistant Examiner* — Timothy P Graves
(74) *Attorney, Agent, or Firm* — Lerner, David, Littenberg, Krumholz & Mentlik, LLP (57) ABSTRACT

The invention concerns a Thickness Shear Mode (TSM) biosensor (1) which comprises an ex vivo living skin explant (2), the skin explant (2) comprising at least one of the skin layers among: hypodermis, dermis (2A), epidermis (2B) and the stratum corneum (2C), a TSM transducer (3) which comprises: an AT cut quartz resonator 3C which has two
(Continued)

opposite exterior surfaces (3A,3B), and two conducting electrodes (4A, 4B), each conducting electrode being deposited on one of the two exterior surfaces (3A,3B), the TSM transducer (3) allowing to determine micro rheological characteristics of the living skin explant (2) by piezoelectric transducing using shear waves, the TSM transducer (3) presenting: measuring means (30), monitoring and calculating means (31) which monitor an evolution in time of an electrical response of the living skin explant (2), and which calculate in time, from the electrical response, micro rheological characteristics of the living skin explant (2), a bottom surface of the skin explant (2) being in contact with the TSM transducer (3), a top surface of the skin explant (2) being in contact with air.

16 Claims, 6 Drawing Sheets

(51) Int. Cl.
G01N 29/036 (2006.01)
G01N 29/028 (2006.01)
(52) U.S. Cl.
CPC ..... *G01N 29/036* (2013.01); *G01N 2291/018* (2013.01); *G01N 2291/0256* (2013.01); *G01N 2291/02483* (2013.01); *G01N 2291/02491* (2013.01); *G01N 2291/02827* (2013.01); *G01N 2291/0426* (2013.01)
(58) Field of Classification Search
CPC ............... G01N 29/028; G01N 29/036; G01N 2291/018; A61B 5/442
See application file for complete search history.

(56) References Cited

U.S. PATENT DOCUMENTS

2014/0197850 A1 7/2014 Serafty et al.
2018/0103852 A1* 4/2018 Dagdeviren ........... G16H 20/17

OTHER PUBLICATIONS

Fang Li,. et al., "An Acoustic Wave Biosensor for Probing the Viscoelastic Properties of Living Cells", Chemical and Biological Sensing VII, vol. 6218, May 19, 2006, (May 19, 2006), XP040224519, 12 pages.
Ehssein C.O. et al, "Kinetic reaction monitoring of acidified milk gels with a quartz resonator : effect of temperature and gdl quantities", 2004 IEEE Ultrasonics Symposium : Aug. 23-27, 2004, Palais Des Congr Gbp Es, Montreal, Canada, IEEE Operations Center. Piscataway. NJ., vol. 1. Aug. 23, 2004 (Aug. 23, 2004), pp. 319-322.
R. F. Rushmer, et. al, "The Skin," Science (80-. ), vol. 154, No. 3747, pp. 343-348, 1966.
C. W. Oomens, et. al, "A mixture approach to the mechanics of skin.," J. Biomech., vol. 20, No. 9, pp. 877-885, 1987.
F. Xu, et. al, "Biothermomechanica/ behavior of skin tissue," Acta Mech. Sin. Xuebao, vol. 24, No. 1, pp. 1-23, 2008.
A. Delalleau, et. al, "Characterization of themechanical properties of skin by inverse analysis combined with the indentation test.," J. Biomech., vol. 39, No. 9, pp. 1603-1610, 2006.
M. J. Koehler, et. al, "In vivo measurement of the human epidermal thickness in different localizations by multiphoton laser tomography," Ski. Res.Techno/., vol. 16, No. 3, pp. 259-264, 2010.
C. Sanchez, et. al, "'Chimie douce': A land of opportunities for the designed construction of functional inorganic and hybrid organic-inorganic nanomaterials," Comptes Rendus Chimie, vol. 13, No. 1-2. pp. 3-39, 2010.
S. Hsu, et. al, "Viscoelastic studies of extracellular matrix interactions in a model native collagen gel system.," Biorheology, vol. 31, No. 1, pp. 21-36, 1994.
X. Liang and S. A. Boppart, "Biomechanical properties of in vivo human skin from dynamic optical coherence elastography," IEEE Trans. Biomed. Eng., vol. 57, No. 4, pp. 953-959, 2010.
B. J. Bell, et. al, "Multiscale strain analysis of tissue equivalents using a custom-designed biaxial testing TSM biosensor," Biophys. J., vol. 102, No. 6, pp. 1303-1312, 2012.
R. B. Groves, et. al, "An anisotropic, hyperelastic model for skin: Experimental measurements, finite element modelling and identification of parameters for 10 human and murine skin," J. Mech. Behav. Biomed. Mater., vol. 18, pp. 167-180, 2013.
J. M. Pereira, et. al, "Dynamic measurement of the viscoelastic properties of skin.," J. Biomech., vol. 24, No. 2, pp. 157-162, 1991.
Z. Del Prete, et. al, "Viscoelastic properties of skin in Mov-13 and Tsk mice," J. Biomech., vol. 37, No. 10, pp. 1491-1497, 2004.
H. G. Vogel, "Directional variations of mechanical parameters in rat skin depending on maturation and age.," J. Invest. Dermatol., vol. 76, No. 6, pp. 493-497, 1981.
O. Lokshin and Y. Lanir, "Viscoelasticity and preconditioning of rat skin under uniaxial stretch: microstructural constitutive characterization.," J. Biomech. Eng., vol. 131, No. 3, p. 031009, 2009.
S. Derler and L. C. Gerhardt, "Tribology of skin: Review and analysis of experimental results for the friction coefficient of human skin," Tribal. Lett., vol. 45, No. 1, pp. 1-27, 2012.
H. A. Wheeler, "Transmission-Line Properties of Parallel Strips Separated by a Dielectric Sheet," IEEE Trans. Microw. Theory Tech., vol. 13, No. 2, pp. 172-185, Mar. 1965.
C. Ould Ehssein,"Systeme instrumental pour la rheologie ultrasonore," Universite de Cergy-Pontoise, 2006.
E. Lopez, et. al, "Calcium improves skin health," House h. Pers. CareToday, vol. 3, pp. 32-35, 2008.
P. Gasser, et. al, "Giycation induction and antiglycation activity of skin care ingredients on living human skin explants.," Int. J. Cosmet. Sci., vol. 33, No. 4, pp. 366-370, Aug. 2011.
P. Leclaire, et. al, "Study ofthe bending modes in circular quartz resonator 3Cs," IEEE Trans. Ultrason. Ferroelectr. Freq.Control, vol. 53, No. 10, pp. 1934-1943, Oct. 2006.
W. Mason,"A Dynamic Measurement of the Elastic, Electric and Piezoelectric constants of Rochelle Salt," Phys. Rev., vol. 55, No. 8, pp. 775-789, Apr. 1939.
G. Sauerbrey, "Verwendung von Schwingquarzen zur Wagung dunner Schichten and zur Mikrowagung," Zeitschrift fOr Phys., vol. 155, No. 2, pp. 206-222, Apr. 1959.
K. Keiji Kanazawa and J. G. Gordon, "The oscillation frequency of a quartz resonator 3C in contact with liquid," Anal. Chim. Acta, vol. 175, No. C, pp. 99-105, 1985.
H. L. Bandey, et. al, "Modeling the Responses ofThickness-Shear Mode Resonators under Various Loading Conditions.," Anal. Chem., vol. 71, No. 11, pp. 2205-2214, Jun. 1999.
A. Arnau, et. al, "Thickness-shear mode quartz crystal resonators in viscoelastic fluid media," J. Appl. Phys., vol. 88, No. 8, p. 4498-4506, 2000.
S. J. Martin, et. al,"Characterization of a Quattz Crystal Microbalance with Simultaneous Mass and Liquid Loading," Anal. Chem., vol. 2281, No. 26, pp. 2272-2281, 1991.
C. Ou/d Ehssein, et. al, "Kinetic study of silica gels by a new rheological ultrasonic investigation," Ultrasonics, vol. 44 Supp/1, pp. e881-e885, Dec. 2006.
A. C. Rowat, et. al, "Interactions of oleic acid and model stratum corneum membranes as seen by 2H NMR," Int. J. Pharm., vol. 307, No. 2, pp. 225-231, 2006.
N. Y. Ryabova, et. al, "Investigation of stratum corneum lipid model membranes with free fatty acid composition by neutron diffraction.," Eur. Biophys. J., vol. 39, No. 8, pp. 1167-1176, 2010.
X. Chen, et. al, "Fatty acids influence 'Solid' phase formation in models of stratum corneum intercellular membranes," Langmuir, vol. 23, No. 10, pp. 5548-5556, 2007.

(56) References Cited

OTHER PUBLICATIONS

D. Lee, et. al, "Permeability of model stratum corneum lipid membrane measured using quattz crystal microbalance," Langmuir, vol. 25, No. 10, pp. 5762-5766, 2009.

* cited by examiner

TSM BIOSENSOR TO EX-VIVO CHARACTERIZE THE VISCOELASTIC PROPERTIES OF SKIN

CROSS REFERENCE TO RELATED APPLICATIONS

The present application is a national phase entry under 35 U.S.C. § 371 of International Application No. PCT/EP2016/063083 filed Jun. 8, 2016, published in English, which claims priority from European Patent Application No. 15306357.3, filed Sep. 3, 2015 and European Patent Application No. 15020088.9, filed Jun. 8, 2015, all of which are incorporated herein by reference.

FIELD OF THE INVENTION

The invention concerns a TSM biosensor to ex-vivo characterize the viscoelastic properties of skin.

STATE OF ART

The skin which comprises dermis, epidermis and the stratum corneum, is a complex biological material similar to layers based on fibers, and on collagen and elastin membranes intermixed and immersed in a fluid, itself complex, in a gel phase (hyaluronic, fibroblasts, proteoglycans, fat and water). The orientation of these fibers and the very thin thickness of these layers imply that the viscoelastic properties of the the skin are often seen as non-linear and anisotropic, and are difficult to characterize either in vivo or ex vivo.

Most commonly used skin samples ex vivo test is the tensile test. Using this method, it is difficult to have homogeneous and reproducible measurements particularly because of non-linear mechanical effects involved, the heterogeneity and variability of the skin.

DESCRIPTION OF DRAWINGS OF THE INVENTION

FIG. 3 shows the modified electrical model used to characterize the viscoelastic properties of skin.
A) TSM Biosensor 1 used for ex-vivo skin characterization (untreated tired skin after dehydration process monitoring): the biosensor 1 consist of two elements: the transducer made of an AT-cut quartz resonator 3C and an ex-vivo skin explant specially designed. B) The electrical model: two parallel branches can independently represent both electrical and mechanical effects. The static branch of impedance $Z_0$ (in gray) includes the dielectric properties of the quartz as a function of the electrical field distribution between the electrodes 4A, 4B; the dynamic branch (motional branch) is representative of the mechanical properties of the quartz $Z_m^0$ and skin ($Z_{load}$).

GENERAL DESCRIPTION OF THE INVENTION

Figure 1:
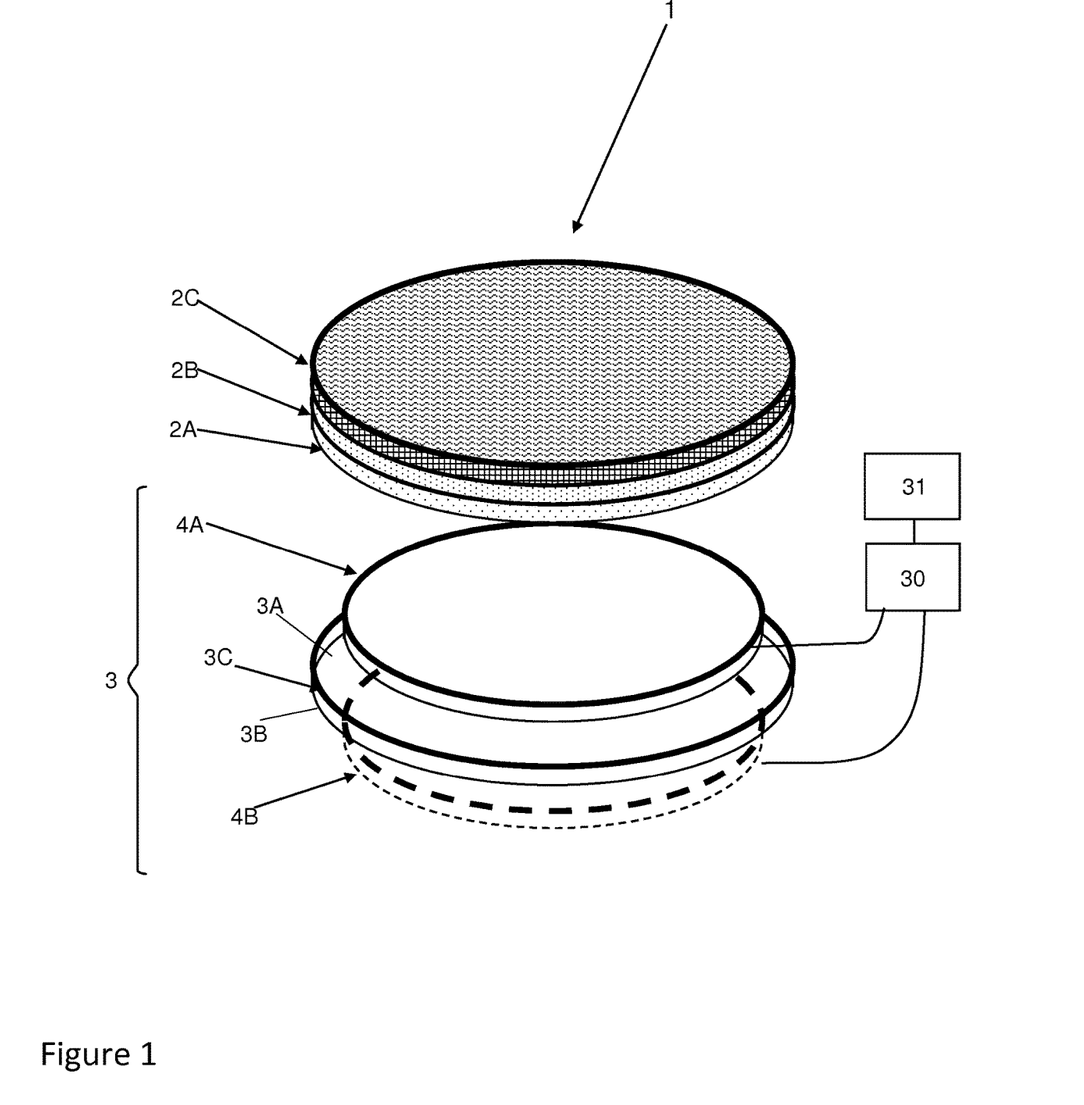
FIG. 1 describes the TSM biosensor of the invention in an exploded view; the different elements of the bio sensor is not to scale.
Figure 2:
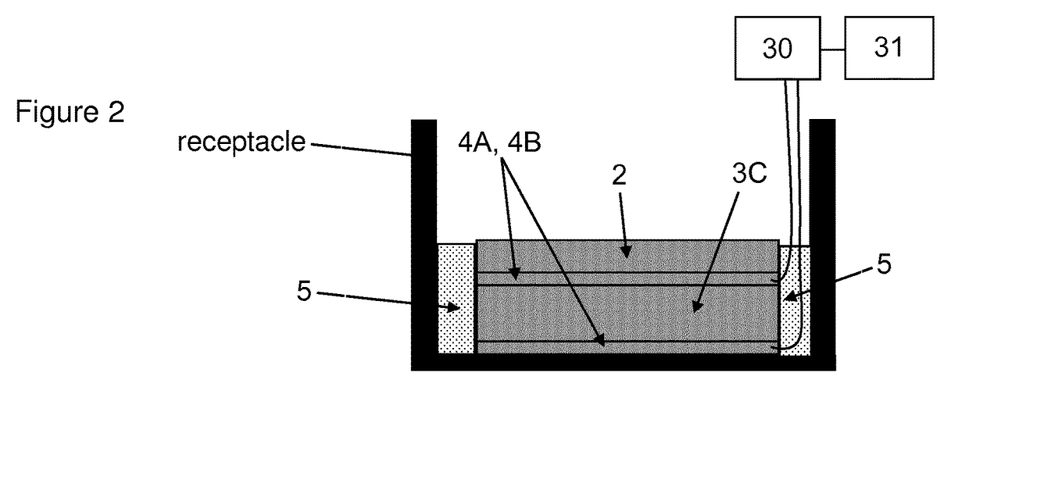
FIG. 2 describes the TSM biosensor of the invention in a sectional view.

The present invention concerns a Thickness Shear Mode (TSM) biosensor 1 which comprises:
- an ex vivo living skin explant 2,
- a TSM transducer 3 which comprises: an AT cut quartz resonator 3C which has two opposite exterior surfaces 3A,3B, and two conducting electrodes 4A, 4B, each conducting electrode being deposited on one of the two exterior surfaces 3A, 3B.

The word 'living' means that the skin explant 2 lives when the measures are realized and has biophysical behavior comparable to the in-vivo skin behavior.

The skin explant can be extracted from a person or an animal with plastic surgery or can be reconstituted with biological cells in an extracellular matrix.

Here the conducting electrodes are in metal, for instance in gold.

In other words, the AT cut quartz resonator 3C represents all the existing quartz crystal piezoelectric substrate used as a shear wave generator and as a thickness shear mode sensor.

The shear waves generated are volume waves.

The wave mode generated is then Thickness Shear Mode (TSM).

The thickness of the quartz resonator 3C is chosen to obtain a frequency resonance at RF range and to generate ultrasound shear waves.

For instance, the fundamental frequency of the quartz resonator 3C used here for the figures is 5 MHz.

The dimensions of the quartz resonator 3C can be determined so that the quartz resonator 3C can have a quality factor Q higher than $10^5$.

The electrodes shape 4A, 4B can be designed in order to optimize the generation wave mode. Here on the FIG. 1, the quartz resonator 3C is a piezoelectric disc with a lateral surface. The shape of electrodes placed at both surfaces of the quartz resonator 3C is also a disc, and advantageously can have the same dimensions and can cover the entire surface of the AT cut quartz resonator 3C.

But the quartz resonator 3C and the electrodes 4A, 4B can have any form.

The electrodes can be for example spiral or other form, in order to be controlled by induction, as described in the patent application WO2012/172253.

Advantageously, the skin explant 2 covers the entire surface of the electrode on which it is deposited.

The TSM transducer 3 allows to measure and convert electrical parameters for determining mechanical characteristics of the living skin explant 2, and can be connected to a computer and a network analyser.

The TSM transducer 3 presents:
measuring means 30,
monitoring and calculating means 31 which monitor an evolution in time of an electrical response of the living skin explant, and which calculate, in time, from the electrical response, micro rheological characteristics of the living skin explant 2.

The skin explant 2 can comprise at least one of the skin layers among: hypodermis, dermis 2A, epidermis 2B and the stratum corneum 2C.

Advantageously, the skin explant 2 comprises a stacking of layers which comprises dermis 2A, epidermis 2B and the stratum corneum 2C, the dermis 2A being in contact with the TSM transducer 3, the stratum corneum 2C being in contact with air.

The layers can comprise a product or can be pretreated before measuring electrical response of the skin explant 2, function of shear waves of the TSM.

Advantageously, the dermis 2A does not need to be glued or stick on the TSM transducer 3, and naturally adheres properly to the TSM transducer 3. Thus, both skin explant 2 and TSM transducer 3 can be considered as a unique device called the TSM biosensor 1. The invention allows to realize an instrumented skin.

It is particularly the case when the electrodes 4A, 4B are in gold and when the dermis 2A is disposed on the electrode just after the preparation and the deposit of the electrode on the substrate resonator.

A bottom surface of the skin explant 2 is in contact with the TSM transducer 3, a top surface of the skin explant 2 being in contact with air, considering a vertical axis perpendicular to the TSM and the skin explant that are horizontally maintained together.

When the skin explant 2 comprises dermis 2A, epidermis 2B and the stratum corneum 2C, a bottom surface of the dermis 2A being in contact with the TSM transducer 3, a top surface of the stratum corneum 2C being in contact with air.

The skin explant 2, in particular the stratum corneum 2C can be treated by a product which is tested.

Figure 3:
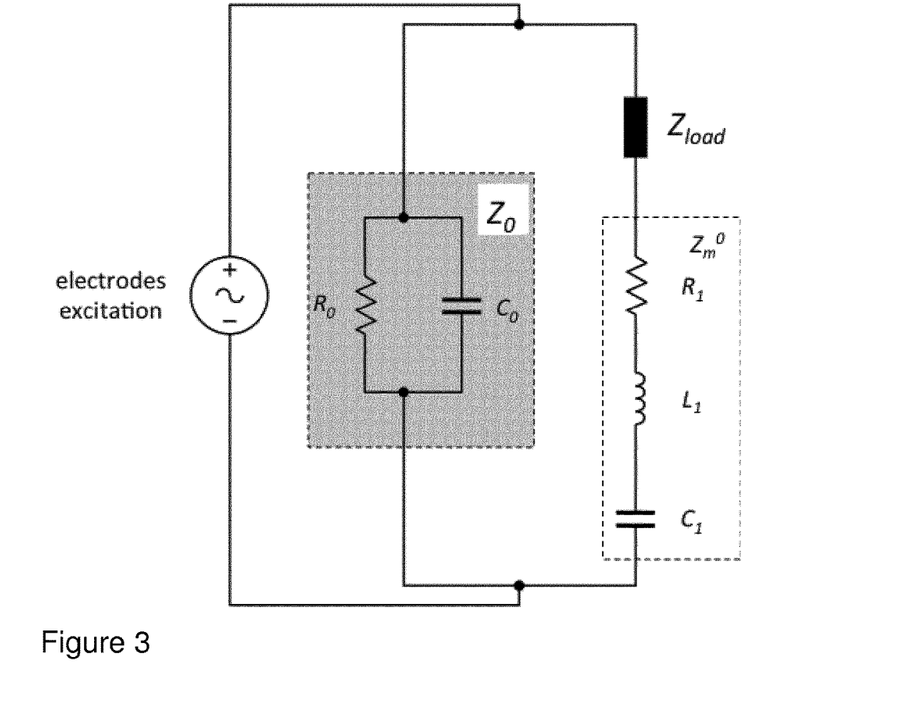

The biosensor 1 is modeled by the modified equivalent electrical lumped elements Butterworth-van-Dyke circuit (BVD) which comprises:
a static branch modeling the electrical behavior of the quartz resonator 3C, and
a dynamic branch parallel to the static branch and modeling the mechanical behavior of the quartz resonator 3C and the mechanical behavior of the living skin explant.

The static branch comprising a resistor and a capacitor connected in parallel.

The dynamic branch comprising in series:
a capacitor, a self-inductance and a resistor modeling the mechanical behavior of the quartz resonator 3C, and
an additional equivalent electrical impedance denoted $Z_{load}=R+j\,X$. This impedance is linked with the complex shear modulus $G=G'+j\,G''$, representative of the living skin explant (2) viscoelasticity at micro-scale, using following equations:

$$R = \frac{h^2}{4A e_q^2} \sqrt{\rho_{skin}\left(\frac{|G(\omega)| + G'(\omega)}{2}\right)}$$

$$X = \frac{h^2}{4A e_q^2}\left(\sqrt{\rho_{skin}\left(\frac{|G(\omega)| - G'(\omega)}{2}\right)} + \omega h_{eff}\right)$$

where h is the thickness of the TSM transducer (excluding the explant thickness), A the surface of the metal electrodes, $e_q$ the piezoelectric constant, $\rho_{skin}$ is the skin density, ω is the resonance pulsation, G', G" are respectively the storage modulus and the loss modulus corresponding to the real and imaginary parts of the complex shear modulus G, and $h_{eff}$ is the depth of living skin.

$Z_{load}$ is the electrical response of the living skin explant 2 and is measured and monitored by the means 30 and 31.

The complex shear modulus G characterizes the micro rheological behaviour of the living skin explant 2.

Figure 8:
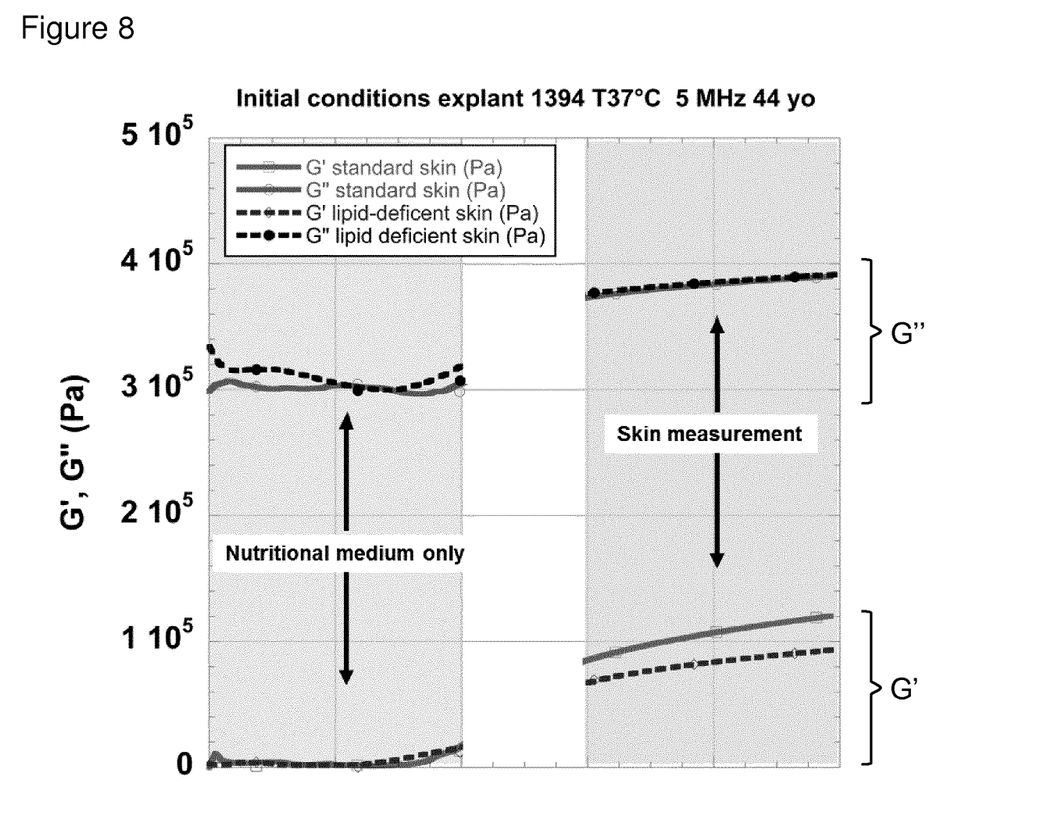
FIG. 8 describes the complex shear modulus $G=G'+j\,G''$, representative of skin viscoelasticity at micro-scale, function of time, for the nutritional medium alone without skin explant (left part of the figure), and with the skin explant (right part of the figure) at 37° C.; the skin explant comes from a 44 years old Caucasian skin donor and the effect of delipidation (dotted line) versus standard skin (solid line) is shown.

The FIG. 8 shows the capacity of the biosensor 1 to measure the skin viscoelasticity (comparison between experiments with nutritional medium only—left part of the figure- and with the living skin explant—right part of the figure) and to observe the effect of skin pretreatments.

Actually the loss modulus G" is identical in presence of nutritional medium whether the living skin explant is delipidated or not delipidated, whereas the storage modulus G' which is representative of the skin elasticity is clearly higher for the standard skin than for the lipid deficient skin (right part of the figure).

In a first embodiment, the TSM transducer 3 comprises a culture medium 5 in contact with at least one of the surfaces of one of the two electrodes 4A, 4B and on which the hypodermis or dermis 2A of the skin explant 2 is in contact with its bottom surface, in order to guarantee the survival of the skin explant 2 on the TSM transducer 3 at least several hours.

In fact, the survival of the skin explant 2 can be ensured several days (more than 10 days, for instance 16 days), depending upon the contact between the culture medium 5 and the skin explant 2, the exterior conditions (temperature . . . ) and the nature of the culture medium 5.

The culture medium 5 is a liquid, a gel, an aerogel, a cream and/or a functionalized layer.

In a first variant of the first embodiment, the culture medium 5 is a gel, an aerogel, or a cream deposited on the surface of one of the two conducting electrodes 4A, 4B.

In a second variant of the first embodiment, the culture medium 5 is a functionalized layer disposed on one of the two conducting electrodes 4A, 4B, and on which the bottom surface of the skin explant 2 is in contact, in order to guarantee the survival of the skin explant 2 on the TSM transducer 3 at least several hours.

In a third variant of the first embodiment, the TSM transducer presents at least one opening which is filled with culture medium 5, allowing the survival of the skin explant 2 during at least several hours or at least several days.

It is possible to realize many openings in the electrode and in the quartz of the TSM transducer and to form like a grid, each opening containing some culture medium 5.

In a second embodiment, the skin explant 2 is moved and removed between the TSM transducer 3 and a receptacle in which there is the culture medium 5. In this second embodiment, the skin explant 2 remains on the TSM transducer only for the measure for instance 15 minutes and is then reintegrated in the receptacle to feed the skin explant 2 and to maintain it alive.

In a third embodiment, the invention concerns also, as drawn on FIG. 2, a device which comprises a TSM biosensor 1 as defined above, and a receptacle in which is deposited the TSM biosensor 1,
the TSM biosensor 1 being surrounded by culture medium 5,
the TSM transducer 3 being immersed in the culture medium 5 so as to maintain the bottom surface of the dermis 2A in the culture medium 5 and the top surface of the stratum corneum 2C in contact with air, allowing the survival of the skin explant 2 during at least several hours or at least several days.

Thus, the TSM biosensor 1 and the receptacle can be sold together, the skin explant 2 being able to survive at least several days.

The invention also concerns a method for determining mechanical characteristics of an ex vivo living skin explant 2, the living skin explant 2 comprising at least one layer among: hypodermis, dermis 2A, epidermis 2B, and the stratum corneum 2C.

The method comprises the following steps:
(a) withdraw a living skin explant 2 from a culture medium 5,
(b) deposit the living skin explant 2 on the TSM transducer 3, a bottom surface of the skin explant 2 being deposited on the TSM transducer 3, a top surface of the skin explant 2 being in contact with air,
(c) measure and monitor electrical parameters for determining and calculating mechanical characteristics of the living skin explant 2.

For instance, the hypodermis or dermis 2A is deposited on the TSM transducer 3, the stratum corneum 2C being in contact with air.

In a step (d) after the step (c), the living skin explant 2 is withdrawn from the TSM transducer 3 and is deposited in the culture medium 5.

In a step (e) after the step (d), the steps (a), (b), (c), (d) are realized again.

In particular, the steps (a), (b), (c), (d) are realized several times during several days.

The living skin explant 2 is pretreated, for instance hydrated or delipidated.

The living skin explant 2 is treated with at least one product, prior to or after its deposition, on the Thickness Shear Mode (TSM) transducer, for monitoring products-to-skin effects.

In the step (b), in a first embodiment, the living skin explant 2 is disposed in contact with one of the two conducting electrodes 4A, 4B.

In the step (b) in a first variant of the first embodiment, the living skin explant 2 is deposited on a gel which comprises culture medium 5, the gel being deposited on one of the two conducting electrodes 4A, 4B.

In the step (b) in a second variant of the first embodiment, the living skin explant 2 is deposited on a functionalized layer with culture medium 5, the functionalized layer being deposited on one of the two conducting electrodes 4A, 4B.

The invention also concerns a use of the TSM biosensor 1 to monitor ex vivo mechanical behavior of the living skin explant 2 and thus to follow its structural evolution function of time, by measuring its viscoelastic characteristics.

In particular, it concerns a use to detect and/or follow skin diseases.

In particular, it concerns a use to analyse and/or study the effect of a product applied to the skin explant 2 or specific treatment.

Example of a New Online Skin Investigation Technique for Tracking Products-to-Skin Mechanical Effects which Concerns Delipidated Skin and Hydrated Skin with a Special Treatment Cream-Based Application Ex-vivo abdominal skin explants 2 from plastic surgery and kept alive are used for this study. Considering the skin as a complex fluid made of membrane and fiber structures immersed in liquid, its mechanical response of a bulk thickness shear wave excitation (ie stress-strain analysis) involves both a viscous component associated with energy dissipation and an elastic component associated with energy storage. A tight monitoring of these two components from the response of a TSM sensor (based on an AT cut quartz resonator 3C at 5 MHz) in contact to the dermis 2A of the ex-vivo explant give us access to the complex dynamic shear moduli (G' and G") evolution of the skin; The appropriate mechanical model describing the sensor response vs shear waves/matrix interactions allows investigating the impact of the product (or treatment) to the viscoelastic properties of the skin.

The complex study of the TSM response in time domain permits a control a) of the dehydration evolution at 37° C. due to interpenetrated intercellular lipid membranes matrix including the first step of permeation process from dermis 2A to Stratum corneum 2C (SC); b) the impact on the kinetics of the permeation process by a product applied at the SC surface. This information includes the structure and properties evolution of the collagen and elastic fibers and the proteoglycans located in the skin. A comparison of mechanical results with other techniques in the literature confirms the validity of the model. These preliminary results show that our TSM technique can be an appreciable new way for ex-vivo skin investigation for test and optimization of new cosmetic products.

Skin is a material of four main complex biological layers (epidermis 2B, dermis 2A, hypodermis or stratum corneum 2C) principally based on interconnected collagen and elastin fibers embedded in a gel-like mixture of fluids (hyaluronic, fibroblasts, proteoglycans, fat and water) [1]-[3]. From a mechanical point of view, skin can be considered as a viscoelastic complex fluid based on membranes and fibers immersed in a liquid [4], [5]. On these conditions, its properties can be characterized as nonlinear and anisotropic soft hybrid complex material or elastomers [6]-[11]. On one hand, the skin viscoelasticity can be mainly attributed to interaction between the interpenetrated elastin—collagen fibers and the liquid mixture. On the other hand the anisotropy behavior is the result of the preferential orientation of collagen beams and residual in-vivo skin stress [12]-[14]. Different non-invasive testing are used to characterize and macroscopically detect skin diseases [15]. Using motional stress on ex-vivo sample, the linear viscoelasticity measurement can be more easily reached. The most commonly used for ex vivo skin samples test is the tensile test. Using this method, the nonlinear effects and viscoelastic behavior of animal skin have been mostly pointed out [16]-[19]. Many other difficulties to perform homogeneous measurements exist because skin structure heterogeneity and the large variability between samples. To date other experimental methods based on stress-strain measurement are largely described in the literature. Some of them are based on measurements of torsion and deformation generated by ultrasound wave propagation. A recent review describe the relevant results available in the literature [20]. They can give access to the linear viscoelasticity of the skin at different scale depending on the wavelength.

A high frequency rheological technique added to a suitable model is used to monitor the complex shear modulus G (related to viscoelasticity) of skin. The technique uses a biosensor 1 made of a Thickness Shear Mode (TSM) resonator (as a transducer) in contact to the dermis 2A of skin. Both transducer and material are then considered as an equivalent lossy TSM biosensor 1. Using an original approach based on Wheeler analysis for lossy micro-strip, this model gives access to mechanical evolution of skin considered as a heterogeneous complex fluid [21], [22].

In order to determine the impact of the skin dehydration to ultrasonic shear wave interactions, the responses of the TSM resonator loaded by different skins and treatments are studied.

The TSM Experimental Setup for Ex-Vivo Skin Monitoring

Ex-Vivo Samples

Ex-vivo human skin samples of 5 mm thickness were prepared from abdominal biopsies (healthy plastic surgeries) of two male donors of respectively 36 years old with Negroid skin and 44 years old with Caucasian skin. In order to study the 3 first layers (from stratum corneum 2C (SC) to dermis 2A layer) the subcutaneous fat is removed from the skin.

Circular explants of 10 mm of diameter are cut out in order to embed each sample with a quartz crystal piezoelectric substrate (described in the following section) used as a shear wave generator and thickness shear mode sensor. Human skin explants 2 were maintained in survival on grids, in plates containing 2 mL special BIO-EC medium (BEM: medium from BIO-EC Laboratory, France). BEM maintain explants in survival for several days, about 20 days [24].

Circular explants preparation: A) circular cut out for embedded biosensing, B) Human skin maintained in survival ready for treatment.

The samples from each donor are prepared in order to study the sensitivity of the new biosensor 1 versus skin hydration treatment. 3 type of treated skin are then studied: A) untreated skin used as the reference; B) delipidated skin; C) Hydrated skin with a special treatment cream-based application. Experiments were performed in triplicate The tested products and treatments were applied on explants as soon as their preparation. Treated and untreated skin explants 2 were incubated at 37° C. in a normal atmosphere conditions. To monitor the dehydration process, a protective film is deposited at the surface of skin. This film ensures a standard skin hydration. As long as the film is present the hydration conditions remain unchanged.

TSM Biosensor 1 for Skin Characterization

The TSM biosensor 1 consists of a thin disk of AT-cut quartz with metal electrodes 4A, 4B deposited on both sides (the resonator) in contact on one side with the dermis 2A of the ex-vivo human skin sample. The diameters of the crystal and the electrode are respectively 14 mm and 5 mm. The quartz thickness of 270 µm provide a resonance frequency about 5 MHz. Considering the piezoelectric properties of the quartz disk, its crystal orientation, the shape of electrodes 4A, 4B, and the electric field applied between the electrodes 4A, 4B, a specific deformation of the crystal surface can be induced. The AT cut of 35° 10' involves maxima shear displacements at the surfaces [25].

Electro-mechanical models already describe the complete oscillations process of the resonator. They are derived from piezoelectric constitutive equations. A general one dimensional acoustic wideband model has been suggested by Mason [26]. In particular cases, such as low load, the Mason model can be easily simplified near the resonant frequencies into an equivalent electrical lumped elements Butterworth-van-Dyke circuit (BVD) [27].

When the sensor is loaded by a rigid layer or a liquid, the mass of the layer in contact involves a frequency shift [28], [29]. Moreover the mechanical boundary conditions including skin loading are modified by the rheological properties of skin. These conditions induce an additional frequency shift and a damping of the resonance corresponding to an attenuation and a delay of the propagated ultrasonic shear waves [30]-[32].

$Z_{load} = R + j\ X$ is representative of these changes. The variation of the electrical response can then accurately extract G, using the following expression [33]-[35].

$$R \cong K\rho_{skin}\sqrt{\frac{(|G(\omega)| + G'(\omega))}{2\rho_{skin}}} \quad (1)$$

$$X \cong K\rho_{skin}\left(\sqrt{\frac{(|G(\omega)| - G'(\omega))}{2\rho_{skin}}} + \omega h_{eff}\right)$$

where K is the electro-mechanical coupling factor, $\rho_{skin}$ is the skin density (1.1 g/cm$^3$), ω is the angular resonance frequency and G', G" are respectively the storage modulus and the loss modulus corresponding to the real and imaginary parts of the complex shear modulus G and $h_{eff}$ is the depth of living skin. Note that the mass effect (at the resonance frequency) only depends on the product skin density—effective thickness of wave penetration.

Experimental Setup

Figure 4:
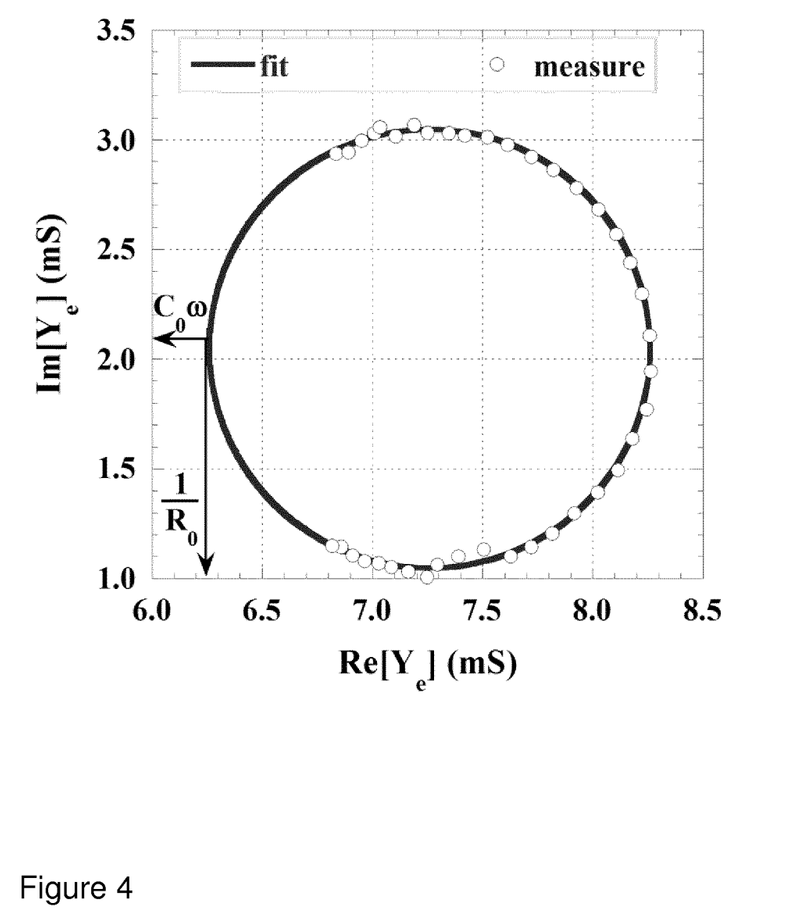
FIG. 4 shows typical fit of the total admittance of the TSM biosensor 1 corresponding to the 3rd order theoretical electrical complex function corresponding to the electrical circuit.

The experimental set-up consists of an impedance analysis of the biosensor 1 during skin dehydration. In order to study the effect of treatments each sample is monitored at controlled temperature (37° C.) using a laboratory oven. Considering the high Q factor of TSM resonator, the admittance measurement is preferred. A span of 7 kHz around the resonance frequency is then analyzed to measure the total admittance response $Y_e(\omega)$ of loaded biosensor 1 using the HP4195A network analyzer. 400 spectral points are then regularly measured in less than 50 seconds. An online fit of this response is performed in the complex plan to extract the real and the imaginary part of $Z_{load}$. The viscoelastic characteristics of skin can be then extracted.

In order to observe the temporal evolution, the frequency response of the admittance is then sampled every minute.

Skin Dehydration Monitoring Using Micro-Rheology Testing

In order to study the sensitivity of the biosensor 1 and to validate the proof of concept of a new technique to monitor the hydration of ex-vivo skin explants 2, 3 type of treatment are explored: untreated skin, hydrated skin, and delipidated skin.

Mass Effect and Rigid Structure Sensitivity

Figure 5:
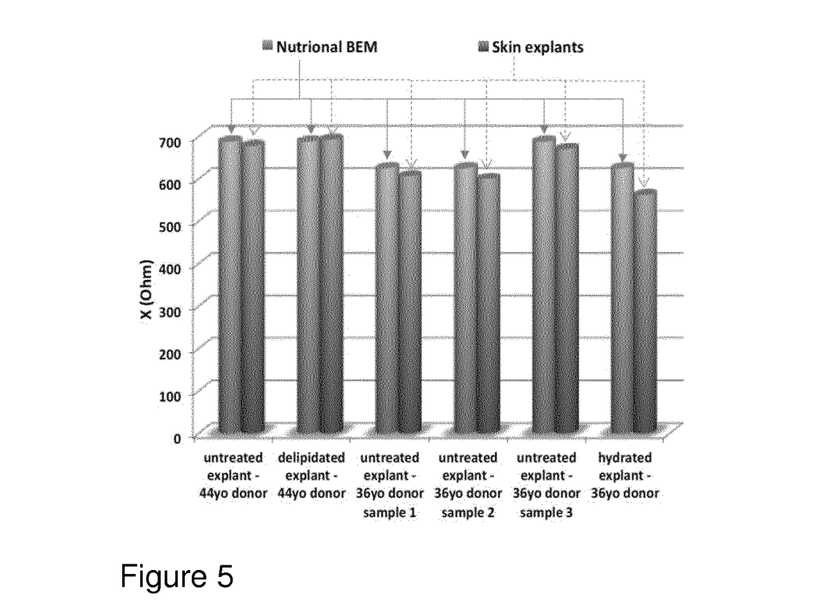
FIG. 5 describes the Mass effect skin explant 2 vs nutritional BEM: The total admittance X is compared for different samples. The mass effect is principally due to the liquid stored in the dermis 2A and epidermis 2B.

To accurately monitor R and X variation due to the viscoelastic effects during the dehydration, the mass effect due to the liquid embedded in the epidermis 2B and dermis 2A is firstly studied. Transducers (without skin explant 2s) are firstly characterized to extract the unloaded motional elements. This measurement gives access to characteristic parameters of unperturbed transducers. A measurement of theses transducers loaded by nutritional BEM liquid is after performed. Considering that this liquid is a Newtonian liquid (G' 0), the mass effect can be directly extracted from the two first measurements (variation of unperturbed transducer admittance and transducer loaded with BEM liquid). Assuming equation 1, the real part of $Z_{load}$ allows the extraction of the viscosity from viscous modulus G". As a consequence, the following substation gives the mass effect ($X_m$):

$$X_m = Im[Z_L] - Re[Z_L] = K\rho_{skin}\omega h_{eff}$$

Comparing the real and the imaginary part of $Z_{load}$ for each measurement the typical mass effect can be estimated to $X_m=10\Omega$. This first result shows that the total reactance is principally due to viscoelastic variation ($X_m/X<1\%$). The FIG. 5 shows the variability of the total reactance and the effect of skin fibers in comparison with BEM.

At the initial conditions, the total reactance X for skin load is similar to the BEM load. In agreement with the literature of skin tribology, skin can be considered as a viscous complex fluid having a viscosity mainly due to the liquid characteristic. The density of skin can be considered close to liquid density. This result is in concordance with the fact that the dermis 2A is continuously supplied with water mixture by way of the bloodstream. In the dermis 2A, a part of the liquid mixture is present in gel phase, attached to many hydrophilic macromolecules. Despite the large capacity of these molecules to capture water mixture, a part of it remains mobile and diffuses to upper layers of skin. Note that the reactance of the transducer loaded by the skin is slightly lower in proportion to the surface in contact with the load.

Figure 6:
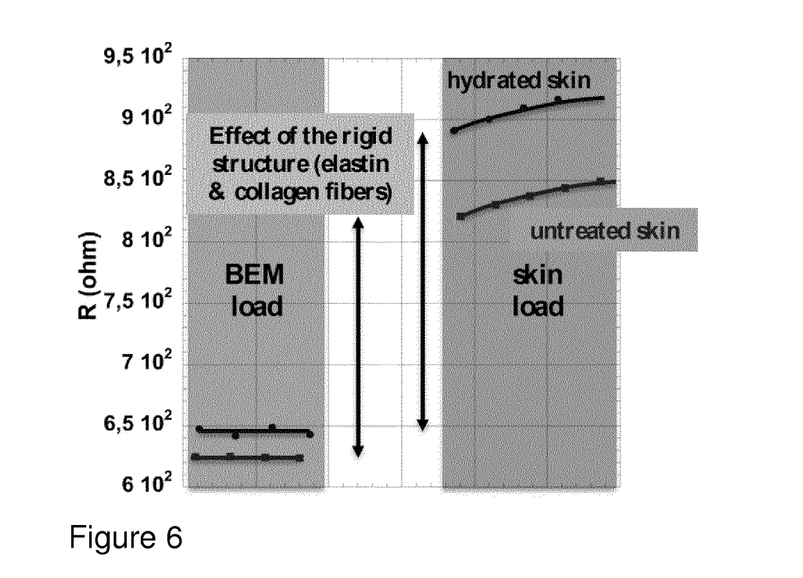
FIG. 6 is a comparison of R load for the 36 yo donor: for BEM load (left) and skin load (right).

In contrast, while the imaginary part remains constant, the real part of impedance load R increases significantly as shown in the FIG. 6.

Considering the equation 1, this variation is due to the interactions of the macromolecules forming a rigid ultra-structure based on elastin and collagen fibers immersed in fat and liquid. The variation of R gives us access to elasticity of skin during dehydration. It can also be observed that allows for better interpenetration of layers increasing the rigidity as shown in FIG. 1.

Dehydration Kinetic Monitoring

Figure 7:
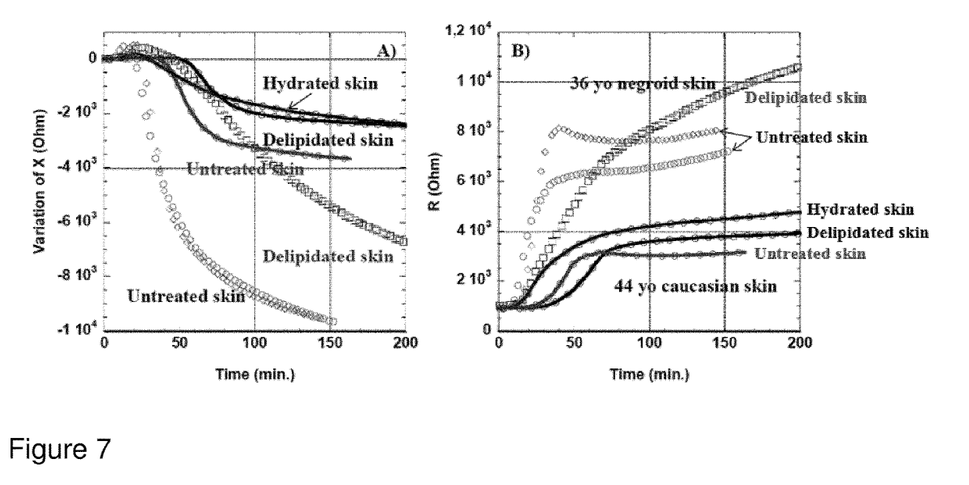
FIG. 7 describes the kinetic of dehydration at 37° C., 22% Hygrometry for Negroid (points only) and Caucasian (line style) treated skins: A) Relative variation of imaginary part of Zload; B) 44 yo Caucasian skin donor.

The intercellular SC lipid membranes play a crucial role in regulating the loss of intrinsic liquid from the skin. This process is in fact directly correlated with SC membranes permeability to this aqueous liquid. SC monitoring using X-ray scattering spectroscopy and NMR studies generally this process [36]-[38]. In order to preliminary study the capability of our technique to monitor the dehydration process, different treatments of ex-vivo human skin are tested. The FIG. 7 shows typical variation of X for treated an untreated skin from the two donors.

The initial time (t=0) is the moment from which the protective film is removed. As a general shape, we note an already known exponential decrease due to the diffusivity of liquid vapor in the lipid membrane. In agreement with one-dimensional diffusion model, this result is also observed by an indirect relative humidity measurement in the QCM chamber as a function of time [39]. The FIG. 7A) shows the repeatability of the technique (untreated skin). The kinetic characteristic time is clearly modified as a function of skin treatment. The long kinetic of dilapidation skin shows the role of lipids in dehydration. In addition the real part of $Z_{load}$ (FIG. 7B) for this treatment shows the skin stiffening due to the interactions of macromolecules. Comparing the effect of different treatments our technique can detect their structure modification and their efficiency. A systematic study should allow cosmetic product optimizing and effectiveness evidence.

The TSM biosensor 1 allows a monitoring of ex-vivo human skin for treatment testing with a large dynamical range. The first results show that it is possible to completely follow the viscoelastic parameters evolution for dehydration monitoring or structure monitoring of skin from stratum corneum 2C to dermis 2A. From the temporal evolution of real and imaginary part of impedance load the effect of skin treatment to the skin layers structure and mechanical properties can be detected. This preliminary study shows that this technique can be suitable to accessing to the elastic G' and viscous G" moduli by micro-rheology. This new biosensor 1 added with our model should become a sensitive ex-vivo technique for cosmetic product efficiency and skin objective testing.

REFERENCES

[1] R. F. Rushmer, K. J. K. Buettner, J. M. Short, and G. F. Odland, "*The Skin,*" *Science* (80-.), vol. 154, no. 3747, pp. 343-348, 1966.

[2] G. Odland, "*Structure of the skin,*" in *Physiology, Biochemistry, and Molecular Biology of the Skin*, 1991, pp. 3-62.

[3] C. W. Oomens, D. H. van Campen, and H. J. Grootenboer, "*A mixture approach to the mechanics of skin.,*" *J. Biomech.*, vol. 20, no. 9, pp. 877-885, 1987.

[4] F. Xu and T. Lu, "*Introduction of Skin Biothermomechanics,*" in *Introduction to Skin Biothermomechanics and Thermal Pain*, 2011, pp. 209-220.

[5] F. Xu, T. J. Lu, and K. A. Seffen, "*Biothermomechanical behavior of skin tissue,*" *Acta Mech. Sin. Xuebao*, vol. 24, no. 1, pp. 1-23, 2008

[6] F. Xu and T. J. Lu, "*Chapter 3 Skin Biothermomechanics: Modeling and Experimental Characterization,*" in *Advances in Applied Mechanics*, volume 43, 2009, pp. 147-248.

[7] F. Xu, T. J. Lu, and K. A. Seffen, "*Biothermomechanics of skin tissues,*" *J. Mech. Phys. Solids*, vol. 56, no. 5, pp. 1852-1884, 2008.

[8] A. Delalleau, G. Josse, J.-M. Lagarde, H. Zahouani, and J.-M. Bergheau, "*Characterization of the mechanical properties of skin by inverse analysis combined with the indentation test.,*" *J. Biomech.*, vol. 39, no. 9, pp. 1603-1610, 2006.

[9] M. J. Koehler, T. Vogel, P. Elsner, K. König, R. Bückle, and M. Kaatz, "*In vivo measurement of the human epidermal thickness in different localizations by multiphoton laser tomography,*" *Ski. Res. Technol.*, vol. 16, no. 3, pp. 259-264, 2010.

[10] C. Sanchez, L. Rozes, F. Ribot, C. Laberty-Robert, D. Grosso, C. Sassoye, C. Boissiere, and L. Nicole, "'*Chimie douce': A land of opportunities for the designed construction of functional inorganic and hybrid organic-inorganic nanomaterials,*" *Comptes Rendus Chimie*, vol. 13, no. 1-2. pp. 3-39, 2010.

[11] S. Hsu, A. M. Jamieson, and J. Blackwell, "*Viscoelastic studies of extracellular matrix interactions in a model native collagen gel system.,*" *Biorheology*, vol. 31, no. 1, pp. 21-36, 1994.

[12] X. Liang and S. A. Boppart, "Biomechanical properties of in vivo human skin from dynamic optical coherence elastography," IEEE Trans. Biomed. Eng., vol. 57, no. 4, pp. 953-959, 2010.

[13] B. J. Bell, E. Nauman, and S. L. Voytik-Harbin, "*Multiscale strain analysis of tissue equivalents using a custom-designed biaxial testing TSM biosensor,*" *Biophys. J.*, vol. 102, no. 6, pp. 1303-1312, 2012.

[14] R. B. Groves, S. A. Coulman, J. C. Birchall, and S. L. Evans, "*An anisotropic, hyperelastic model for skin: Experimental measurements, finite element modelling and identification of parameters for human and murine skin,*" *J. Mech. Behav. Biomed. Mater.*, vol. 18, pp. 167-180, 2013.

[15] J. Serup, G. B. E. Jemec, and G. L. Grove, *Handbook of Non-Invasive Methods and the Skin, Second Edition*—, CRC Press. 2006.

[16] J. M. Pereira, J. M. Mansour, and B. R. Davis, "*Dynamic measurement of the viscoelastic properties of skin.,*" *J. Biomech.*, vol. 24, no. 2, pp. 157-162, 1991.

[17] Z. Del Prete, S. Antoniucci, A. H. Hoffman, and P. Grigg, "*Viscoelastic properties of skin in Mov-13 and Tsk mice,*" *J. Biomech.*, vol. 37, no. 10, pp. 1491-1497, 2004.

[18] H. G. Vogel, "*Directional variations of mechanical parameters in rat skin depending on maturation and age.,*" *J. Invest. Dermatol.*, vol. 76, no. 6, pp. 493-497, 1981.

[19] O. Lokshin and Y. Lanir, "*Viscoelasticity and preconditioning of rat skin under uniaxial stretch: microstructural constitutive characterization.,*" *J. Biomech. Eng.*, vol. 131, no. 3, p. 031009, 2009.

[20] S. Derler and L. C. Gerhardt, "*Tribology of skin: Review and analysis of experimental results for the friction coefficient of human skin,*" *Tribol. Lett.*, vol. 45, no. 1, pp. 1-27, 2012.

[21] H. A. Wheeler, "*Transmission-Line Properties of Parallel Strips Separated by a Dielectric Sheet,*" *IEEE Trans. Microw. Theory Tech.*, vol. 13, no. 2, pp. 172-185, March 1965.

[22] C. Ould Ehssein, "*Système instrumental pour la rhéologie ultrasonore,*" Université de Cergy-Pontoise, 2006.

[23] E. Lopez, E. Latie, P. Gasser, and M. Rousseau, "*Calcium improves skin health,*" *Househ. Pers. Care Today*, vol. 3, pp. 32-35, 2008.

[24] P. Gasser, F. Arnold, L. Peno-Mazzarino, D. Bouzoud, M. T. Luu, E. Lati, and M. Mercier, "*Glycation induction and antiglycation activity of skin care ingredients on living human skin explants.,*" *Int. J. Cosmet. Sci.*, vol. 33, no. 4, pp. 366-70, August 2011.

[25] P. Leclaire, J. Goossens, L. Martinez, N. Wilkie-Chancelier, S. Serfaty, and C. Glorieux, "*Study of the bending modes in circular quartz resonator 3Cs,*" *IEEE Trans. Ultrason. Ferroelectr. Freq. Control*, vol. 53, no. 10, pp. 1934-1943, October 2006.

[26] W. Mason, "*A Dynamic Measurement of the Elastic, Electric and Piezoelectric Constants of Rochelle Salt,*" *Phys. Rev.*, vol. 55, no. 8, pp. 775-789, April 1939.

[27] R. W. Cernosek, S. J. Martin, A. R. Hillman, and H. L. Bandey, "*Comparison of lumped-element and transmission-line models for thickness-shear-mode quartz resonator 3C sensors,*" *IEEE Trans. Ultrason. Ferroelectr. Freq. Control*, vol. 45, no. 5, pp. 1399-1407, September 1998.

[28] G. Sauerbrey, "*Verwendung von Schwingquarzen zur Wägung dünner Schichten and zur Mikrowägung,*" *Zeitschrift für Phys.*, vol. 155, no. 2, pp. 206-222, April 1959.

[29] K. Keiji Kanazawa and J. G. Gordon, "*The oscillation frequency of a quartz resonator 3C in contact with liquid,*" *Anal. Chim. Acta*, vol. 175, no. C, pp. 99-105, 1985.

[30] H. L. Bandey, S. J. Martin, R. W. Cernosek, and A. R. Hillman, "*Modeling the Responses of Thickness-Shear Mode Resonators under Various Loading Conditions.,*" *Anal. Chem.*, vol. 71, no. 11, pp. 2205-14, June 1999.

[31] A. Arnau, Y. Jiménez, and T. Sogorb, "*Thickness-shear mode quartz crystal resonators in viscoelastic fluid media,*" *J. Appl. Phys.*, vol. 88, no. 8, p. 4498, 2000.

[32] S. J. Martin, V. E. Granstaff, and G. C. Frye, "*Characterization of a Quartz Crystal Microbalance with Simultaneous Mass and Liquid Loading,*" *Anal. Chem.*, vol. 2281, no. 26, pp. 2272-2281, 1991.

[33] C. O. Ehssein, S. Serfaty, P. Griesmar, E. Caplain, L. Martinez, and M. Gindre, "*Kinetic reaction monitoring of acidified milk gels with a quartz resonator 3C: effect of temperature and gdl quantities,*" in *IEEE Inter. Ultrasonics, Ferroelectric, and Frequency Controls, 50th Conf.*, 2004, vol. 1, pp. 319-322.

[34] E. Caplain, C. Quid Ehssein, S. Serfaty, L. Martinez, J.-Y. Le Huérou, and M. Gindre, "*Toward embedded viscosimeter using quartz crystal resonator,*" in *3rd Meeting IEEE Sensors*, Vienna, Austria, 2004, p. octobre-octobre.

[35] C. Quid Ehssein, J. Y. Le Huerou, L. Martinez, E. Caplain, N. Wilkie-Chancellier, M. Gindre, G. Gouedard, and P. Figuiere, "*Kinetic study of silica gels by a new rheological ultrasonic investigation,*" *Ultrasonics*, vol. 44 Suppl 1, pp. e881-5, December 2006.

[36] A. C. Rowat, N. Kitson, and J. L. Thewalt, "*Interactions of oleic acid and model stratum corneum membranes as seen by 2H NMR,*" *Int. J. Pharm.*, vol. 307, no. 2, pp. 225-231, 2006.

[37] N. Y. Ryabova, M. A. Kiselev, S. Dante, T. Hauss, and A. M. Balagurov, "*Investigation of stratum corneum lipid model membranes with free fatty acid composition by neutron diffraction.,*" *Eur. Biophys. J.*, vol. 39, no. 8, pp. 1167-1176, 2010.

[38] X. Chen, S. Kwak, M. Lafleur, M. Bloom, N. Kitson, and J. Thewalt, "*Fatty acids influence 'Solid' phase formation in models of stratum corneum intercellular membranes,*" *Langmuir*, vol. 23, no. 10, pp. 5548-5556, 2007.

[39] D. Lee, J. N. Ashcraft, E. Verploegen, E. Pashkovski, and D. A. Wertz, "*Permeability of model stratum corneum lipid membrane measured using quartz crystal microbalance,*" *Langmuir*, vol. 25, no. 10, pp. 5762-5766, 2009.

The invention claimed is:

1. A receptacle comprising:
a Thickness Shear Mode (TSM) biosensor;
a culture medium; and
an ex vivo living skin explant in contact with the culture medium, the skin explant comprising dermis, epidermis and stratum corneum,
wherein the TSM biosensor comprises:
a TSM transducer comprising: an AT cut quartz resonator, wherein the AT cut quartz resonator has two opposite exterior surfaces, and two metal electrodes, each metal electrode being deposited on one of the two exterior surfaces,
the TSM transducer allowing to measure and to convert electrical parameters for determining mechanical characteristics of the living skin explant, and being configured to generate TSM waves into the ex vivo living skin explant,
the dermis being in contact with the TSM transducer, the stratum corneum being in contact with air, and
wherein the TSM biosensor is surrounded by the culture medium, the TSM transducer is immersed in the culture medium so as to maintain the dermis in the culture medium and the stratum corneum in contact with air, allowing the survival of the skin explant during at least several hours.

2. A receptacle according to claim 1, wherein the culture medium is disposed on one of the two electrodes, and wherein the dermis of the skin explant is in contact with said electrode, in order to guarantee the survival of the skin explant on the TSM transducer at least several hours.

3. A receptacle according to claim 1, wherein the culture medium is a gel.

4. A receptacle according to claim 2, wherein the culture medium (5) provides additional function beyond providing nutrient support for the skin explant.

5. A receptacle according to claim 1, wherein the electrode in contact with the ex vivo living skin explant has at least one opening which is filled with the culture medium, allowing the survival of the skin explant during at least several hours.

6. A receptacle according to claim 1, wherein the electrodes cover the entire surface of the AT cut quartz resonator.

7. A receptacle according to claim 1, wherein the skin explant covers the entire surface of one electrode on which it is deposited.

8. A receptacle according to claim 1, wherein the electrodes are made of gold.

9. A receptacle comprising:
a culture medium,
a Thickness Shear Mode (TSM) biosensor; and
an ex vivo living skin explant in contact with the culture medium, the skin explant comprising dermis, epidermis and stratum corneum,
wherein the TSM biosensor comprises a TSM transducer which comprises an AT cut quartz resonator, wherein the AT cut quartz resonator has two opposite exterior surfaces and two metal electrodes, each metal electrode being deposited on one of the two exterior surfaces,
the TSM transducer allowing to measure and to convert electrical parameters for determining mechanical characteristics of the living skin explant, and being configured to generate TSM waves into the ex vivo living skin explant,
the dermis being in contact with the TSM transducer, the stratum corneum being in contact with air, and
wherein the TSM transducer comprises a monitoring system with monitoring and calculating means which give access to an additional equivalent electrical impedance of the TSM biosensor loaded by the living skin explant, denoted Z=R+j X, Z being linked with the complex shear modulus G=G'+j G", representative of skin viscoelasticity from the modified equivalent electrical lumped elements Butterworth-van-Dyke circuit (BVD), using following equations:

$$R \cong K\rho_{skin}\sqrt{\frac{(|G(\omega)| + G'(\omega))}{2\rho_{skin}}}$$

$$X \cong K\rho_{skin}\left(\sqrt{\frac{(|G(\omega)| - G'(\omega))}{2\rho_{skin}}} + \omega h_{\textit{eff}}\right)$$

where K is the electromechanical coupling factor $\rho_{skin}$ is the skin density, $\omega$ is the resonance pulsation, G', G" are respectively the storage modulus and the loss modulus corresponding to the real and imaginary parts of the complex shear modulus G, and $h_{\textit{eff}}$ is the depth of living skin.

10. A receptacle according to claim 9, wherein the monitoring and calculating means integrate an electrical model of the biosensor by an electrical circuit,
the biosensor being modeled by an electrical circuit which comprises:
a static branch modeling the electrical behavior of quartz, and
a dynamic branch parallel to the static branch and modeling the mechanical behavior of quartz and the mechanical behavior of skin,
the static branch comprising a resistor and a capacitor connected in parallel,
the dynamic branch comprising in series:
a capacitor, a self-inductance and a resistor modeling the mechanical behavior of quartz, and
the additional equivalent electrical impedance Z modeling the mechanical behavior of the skin.

11. Method for determining mechanical characteristics of ex vivo living skin explant being in contact with a culture medium, the living skin explant comprising dermis, epidermis, and stratum corneum, using a TSM transducer which comprises: an AT cut quartz resonator which has two opposite exterior surfaces, and two metal electrodes, each metal electrode being deposited on one of the two exterior surfaces, the method comprising:
(a) putting the dermis in contact with the TSM transducer,
(b) generating, by the TSM transducer, TSM waves into the ex vivo living skin explant,
(c) measuring and converting, by the TSM transducer, electrical parameters for determining mechanical characteristics of the living skin explant,
wherein the TSM transducer is immersed in and surrounded by the culture medium so as to maintain the dermis in the culture medium and the stratum corneum in contact with air, allowing the survival of the skin explant during at least several hours.

12. A method according to claim 11, wherein the living skin explant is hydrated or delipidated.

13. A method according to claim 11, wherein, the living skin explant is treated with at least one product, prior to or after its deposition on the TSM transducer, for monitoring products-to-skin effects.

14. A method according to claim 11 comprising testing ex vivo mechanical behavior of living skin explant and determining viscoelastic characteristics of the living skin explant.

15. A method according to claim 11, comprising detecting and/or following skin diseases to analyse the effect of a product on the skin explant.

16. Method for determining mechanical characteristics of ex vivo living skin explant being in contact with a culture medium, the living skin explant (2) comprising dermis, epidermis, and stratum corneum, using a TSM transducer which comprises: an AT cut quartz resonator which has two opposite exterior surfaces, and two metal electrodes, each metal electrode being deposited on one of the two exterior surfaces, the method comprising:
(a) putting the dermis in contact with the TSM transducer,
(b) generating, by the TSM transducer, TSM waves into the ex vivo living skin explant,
(c) measuring and converting, by the TSM transducer, electrical parameters for determining mechanical characteristics of the living skin explant, wherein the TSM transducer comprises a monitoring system with monitoring and calculating means which give access to an additional equivalent electrical impedance of the TSM biosensor loaded by the living skin explant, denoted Z=R+j X, Z being linked with the complex shear modulus G=G'+j G", representative of skin viscoelasticity from the modified equivalent electrical lumped elements Butterworth-van-Dyke circuit (BVD), using following equations:

$$R \cong K\rho_{skin}\sqrt{\frac{(|G(\omega)| + G'(\omega))}{2\rho_{skin}}}$$

$$X \cong K\rho_{skin}\left(\sqrt{\frac{(|G(\omega)| - G'(\omega))}{2\rho_{skin}}} + \omega h_{\textit{eff}}\right)$$

Where K is the electromechanical coupling factor, $\rho_{skin}$ is the skin density, $\omega$ is the resonance pulsation, G', G" are respectively the storage modulus and the loss modulus corresponding to the real and imaginary parts of the complex shear modulus G, and $h_{e}ff$ is the depth of living skin, the biosensor (1) being modeled by an electrical circuit which comprises:

a static branch modeling the electrical behavior of quartz, and a dynamic branch parallel to the static branch and modeling the mechanical behavior of quartz and the mechanical behavior of skin, the static branch comprising a resistor and a capacitor connected in parallel, the dynamic branch comprising in series:

a capacitor, a self inductance and a resistor modeling the mechanical behavior of quartz, and the additional equivalent electrical impedance Z modeling the mechanical behavior of the skin.

\* \* \* \* \*